US010939876B2

(12) United States Patent
Weiss et al.

(10) Patent No.: US 10,939,876 B2
(45) Date of Patent: Mar. 9, 2021

(54) DEDICATED USER INTERFACE FOR MR-GUIDED INTERSTITIAL INTERVENTIONS

(71) Applicant: KONINKLIJKE PHILIPS N.V., Eindhoven (NL)

(72) Inventors: Steffen Weiss, Hamburg (DE); Thomas Erik Amthor, Hamburg (DE); Sascha Krueger, Hamburg (DE); Daniel Wirtz, Hamburg (DE); Falk Uhlemann, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1284 days.

(21) Appl. No.: 14/408,342

(22) PCT Filed: Jun. 20, 2013

(86) PCT No.: PCT/IB2013/055058
§ 371 (c)(1),
(2) Date: Dec. 16, 2014

(87) PCT Pub. No.: WO2014/001974
PCT Pub. Date: Jan. 3, 2014

(65) Prior Publication Data

US 2015/0148660 A1 May 28, 2015

Related U.S. Application Data

(60) Provisional application No. 61/665,462, filed on Jun. 28, 2012.

(51) Int. Cl.
*A61B 5/00* (2006.01)
*A61B 5/055* (2006.01)
(Continued)

(52) U.S. Cl.
CPC ............ *A61B 5/7405* (2013.01); *A61B 5/055* (2013.01); *A61B 5/7475* (2013.01); *A61B 34/20* (2016.02);
(Continued)

(58) Field of Classification Search
CPC ................................................ A61B 2090/364
See application file for complete search history.

(56) References Cited

U.S. PATENT DOCUMENTS 5,307,808 A * 5/1994 Dumoulin ............ G01R 33/285 600/420
5,943,719 A 8/1999 Feldman
(Continued)

FOREIGN PATENT DOCUMENTS

CN 101564289 A 10/2009
JP 2000262518 A 9/2000
(Continued)

OTHER PUBLICATIONS

Fischbach, F. et al "MR-Guided Ablative Therapy of Malignant Liver Tumors Employing the Panorama HFO Open MR Scanner", Clinical Applications, Medicamundi, vol. 54, No. 3, 2010, pp. 35-40.

(Continued)

*Primary Examiner* — Rajeev P Siripurapu
(74) *Attorney, Agent, or Firm* — Sherry Austin

(57) ABSTRACT

A magnetic resonance (MR) system (10) for guidance of a shaft or needle (16) to a target (14) of a subject (12) is provided. The system includes a user interface (76). The user interface (76) includes a frame (78) positioned on a surface of the subject (12). The frame (78) includes an opening (82) over an entry point of a planned trajectory for the shaft or needle (16). The planned trajectory extends from the entry point to the target (14). The user interface (76) further
(Continued)

76
36, 78
88
80, 84
82
70
16
θ
φ
90
86
TRAJECTORY
90 includes one or more visual indicators (80) arranged on the frame (78) around the opening (82). The one or more visual indicators (80) at least one of: 1) visually indicate deviation of the shaft or needle (16) from the planned trajectory; and 2) visually indicate a current position of a real-time slice of real-time MR images.

15 Claims, 6 Drawing Sheets

(51) Int. Cl.

| | |
|---|---|
| ***A61B 90/30*** | (2016.01) |
| ***G01R 33/28*** | (2006.01) |
| ***A61B 90/00*** | (2016.01) |
| ***A61B 90/11*** | (2016.01) |
| ***A61B 34/20*** | (2016.01) |
| ***A61B 34/00*** | (2016.01) |
| ***G01R 33/341*** | (2006.01) |

(52) U.S. Cl.

CPC .............. *A61B 34/25* (2016.02); *A61B 90/11* (2016.02); *A61B 90/30* (2016.02); *A61B 90/39* (2016.02); *G01R 33/286* (2013.01); *G01R 33/341* (2013.01); *A61B 2034/2074* (2016.02); *A61B 2090/309* (2016.02); *A61B 2090/372* (2016.02); *A61B 2090/374* (2016.02); *A61B 2090/3954* (2016.02)

(56) References Cited

U.S. PATENT DOCUMENTS

| | | | | |
|---|---|---|---|---|
| 6,119,032 | A | 9/2000 | Martin | |
| 6,317,619 | B1 * | 11/2001 | Boernert | G01R 33/341 324/307 |
| 6,605,095 | B2 | 8/2003 | Grossman | |
| 7,302,288 | B1 * | 11/2007 | Schellenberg | A61B 90/36 600/427 |
| 7,876,942 | B2 | 1/2011 | Gilboa | |
| 2005/0245814 | A1 * | 11/2005 | Anderson | A61B 5/06 600/410 |
| 2008/0221520 | A1 | 9/2008 | Nagel | |
| 2010/0036384 | A1 | 2/2010 | Gorek | |
| 2010/0082040 | A1 * | 4/2010 | Sahni | A61B 17/3403 606/130 |
| 2013/0066192 | A1 * | 3/2013 | Sarvestani | A61B 17/3403 600/424 |

FOREIGN PATENT DOCUMENTS

| | | | |
|---|---|---|---|
| JP | 200404428 | A | 2/2004 |
| JP | 2007190199 | A | 8/2007 |
| RU | 2436512 | C1 | 12/2011 |
| WO | 2012062482 | A1 | 5/2012 |
| WO | 2012137148 | A1 | 10/2012 |

OTHER PUBLICATIONS

Wonneberger, U. et al "Clinically Usable Tool for Dynamic Scan-Plane Tracking for Real-Time MRI-Guided Needle Interventions in a High-Field-Open MRI System", Proc. Intl. Society Magnetic Resonance in Medicine, vol. 19, 2011, pp. 202.

Nakamoto et al "Integration of Surgical Planning and Multi-Mode Navigation Improves Accuracy of MR Guided Insertion Procedure" Journal of Japan Society of Computer Aided Surgury vol. 10, No. 1, p. 45-52 (2008) Article and English Abstract.

* cited by examiner

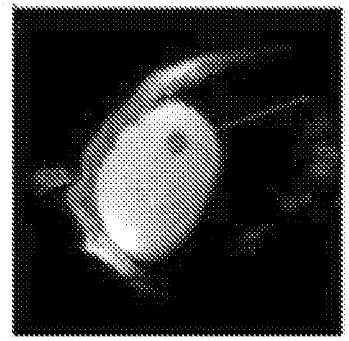
FIG. 4A
FIG. 4B
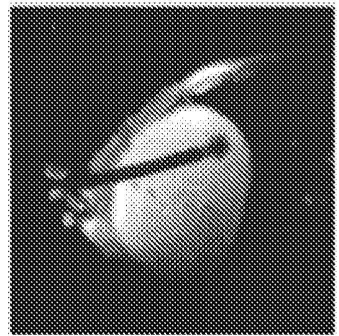
FIG. 4C
FIG. 4D

DEDICATED USER INTERFACE FOR MR-GUIDED INTERSTITIAL INTERVENTIONS

CROSS-REFERENCE TO PRIOR APPLICATIONS

This application is the U.S. National Phase application under 35 U.S.C. § 371 of International Application No. PCT/IB2013/055058, filed on Jun. 20, 2013, which claims the benefit of U.S. Provisional Patent Application No. 61/665,462, filed on Jun. 28, 2012. These applications are hereby incorporated by reference herein.

The following relates generally to magnetic resonance (MR) imaging. It finds particular application in conjunction with MR-guidance and will be described with particular reference thereto. However, it is to be understood that it also finds application in other usage scenarios and is not necessarily limited to the aforementioned application.

The availability of interactive real-time MR imaging and MR-conditional instruments has led to increasing use of MR-guidance, especially in transcutaneous procedures performed with a shaft or needle, such as linear ablation probes. Besides the absence of ionizing radiation, MR-guidance offers a number of advantages over computed tomography (CT)-guidance and ultrasound (US)-guidance for such procedures. Some of the more important advantages includes the soft tissue contrast and full tomographic capability of MR.

State-of-the-art clinical MR-guided percutaneous interventions use pre-operative three-dimensional (3D) MR images to plan the trajectory of the shaft or needle. Therafter, stereotactic device guides are used to align the shaft or needle with the target and to guide its insertion, which is mostly performed outside the MR scanner. Finally, MR is used to confirm that the shaft or needle has reached the target.

Because stereotactic procedures are prone to registration errors from patient motion, organ motion, and needle bending, and because such procedures involve a complicated workflow (e.g., patient movement into and out of the MR scanner), some medical centers are now practicing so-called free-hand procedures in which the shaft or needle is advanced without any physical stereotactic device guide under real-time MR guidance. This is facilitated by dedicated MR sequences that visualize the target and the shaft or needle with high conspicuity and by the availability of open MR systems, though the described approach is not limited to these open bore systems.

For example, in a typical approach for liver biopsy, a subject is positioned within an open MR scanner and ready for liver intervention. The entry point for the interventional instrument may be marked on the skin of the patient. An interventionist then advances a shaft or needle into the subject under real-time MR guidance.

Typically, the workflow of a free-hand procedure includes identification of a target on diagnostic MR images. The trajectory of the shaft or needle is then planned using the diagnostic MR images, and two perpendicular real-time MR imaging slices are selected such that the planned trajectory coincides with the cross-section of the imaging slices. For liver procedures, a para-transversal and a para-coronal slice are typically selected. Thereafter, the shaft or needle is aligned with the planned trajectory outside the subject and then inserted along the planned trajectory under real-time MR guidance. Repeated fine adjustment of the real-time slice positions are made during needle insertion.

The identification, planning and selection steps are typically performed from a console, and the remaining steps are typically performed by the interventionist from the MR scanner. A known procedure for performing these remaining steps is to use one or more active markers to measure the orientation of the shaft or needle with a tracking sequence that can be interleaved with the imaging sequence. However, challenges with this procedure include unintuitive visualization of geometries of the shaft or needle and the planes of the slices, and unintuitive interaction for slice adjustment.

As to visualization of geometries of the shaft or needle and the planes of the slices, the interventionist leans into the MR scanner and maneuvers the shaft or needle with one hand, possibly touching and/or spreading the skin of the subject with the other hand. In doing so, the interventionist's head is tilted, thereby causing discomfort to the interventionist. Further, when the interventionist wants to align the needle with the planned trajectory outside the subject, he continuously must alternate between viewing the shaft or needle and viewing the display device, which is located behind the MR scanner and which displays the real-time MR images and potentially a model of the needle in relation to the pre-operative 3D data including the target. Even more, the interventionist has to mentally translate between the view coordinates at the shaft or needle and the display device. In all, the foregoing requires an experienced interventionist with considerable 3D imagination.

As to interaction for slice adjustment, the interventionist monitors the passive contrast of the shaft or needle, or monitors a model of the shaft or needle based on the marker positions, and the target lesion on the display device, while selecting and adjusting slice positions, which is currently done using a triple foot pedal. Single and double clicks on each pedal are applied to select, shift, rotate and tilt the slices. This also requires the interventionist to imagine the positions of the slices, the shaft or needle, and the target in 3D, which is associated with a learning curve and additional concentration.

The following provides a new and improved system and method which overcome the above-referenced problems and others.

In accordance with one aspect, a magnetic resonance (MR) system for guidance of a shaft or needle to a target of a subject is provided. The system includes a user interface. The user interface includes a frame positioned on a surface of the subject. The frame includes an opening over an entry point of a planned trajectory for the shaft or needle. The planned trajectory extends from the entry point to the target. The user interface further includes at least one of: 1) one or more visual indicators arranged on the frame around the opening; and 2) one or more user input devices arranged on the frame around the opening. The one or more visual indicators at least one of: 1) visually indicate deviation of the shaft or needle from the planned trajectory; and 2) visually indicate a current position of a real-time slice of real-time MR images. The user input devices selectively adjusts the current position of the real-time slice.

In accordance with another aspect, a method for magnetic resonance (MR) guidance of a shaft or needle to a target of a subject is provided. The method includes at least one of: 1) visually indicating how to align the shaft or needle to a planned trajectory; and 2) visually indicating a current position of a real-time slice of real-time MR images. Said visual indicating how to align the shaft or needle to the planned trajectory includes determining a current trajectory of the shaft or needle. The planned trajectory is compared with the current trajectory to determine how to align the shaft or needle to the planned trajectory. The planned trajectory extends from an entry point of the subject to the target. A visual indication as to how to align the shaft or needle to the planned trajectory is generated using a user interface. The user interface is positioned on a surface of the subject and includes an opening over the entry point. Said visual indicating the current position of the real-time slice of the real-time MR images includes displaying the respective real-time MR image on a display device. A visual indication as to the current position of the real-time slice is generated using the user interface. One or more light sources of the user interface indicate where the plane of the real-time slice intersects the frame.

In accordance with another aspect, an apparatus operating in conjunction with an interventional instrument providing real time imaging for guiding a shaft or needle to a target of a subject is provided. The apparatus includes a frame positioned on a surface of the subject. The frame includes an opening over an entry point of a planned trajectory for the shaft or needle extending from the entry point to the target. The frame further includes one or more visual indicators arranged on the frame around the opening. The apparatus further includes at least one processor programmed to operate the one or more visual indicators on the frame to visually indicate at least one of: (i) a current position of the real time imaging slice; and (ii) deviation of the current position of the shaft or needle from the planned trajectory.

One advantage resides in intuitive visualization of geometries of the deviation of the current position of the shaft or needle from the planned trajectory and of the planes of the slices.

Another advantage resides in intuitive interaction for slice adjustment.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 4A illustrates a slice of a real-time MR image of a subject before insertion of a shaft or needle into the subject.

FIG. 4B illustrates another slice of the real-time MR image of FIG. 4A.

FIG. 4C illustrates a slice of a real-time MR image of a subject after insertion of a shaft or needle into the subject.

FIG. 4D illustrates another slice of the real-time MR image of FIG. 4C.

Figure 1:
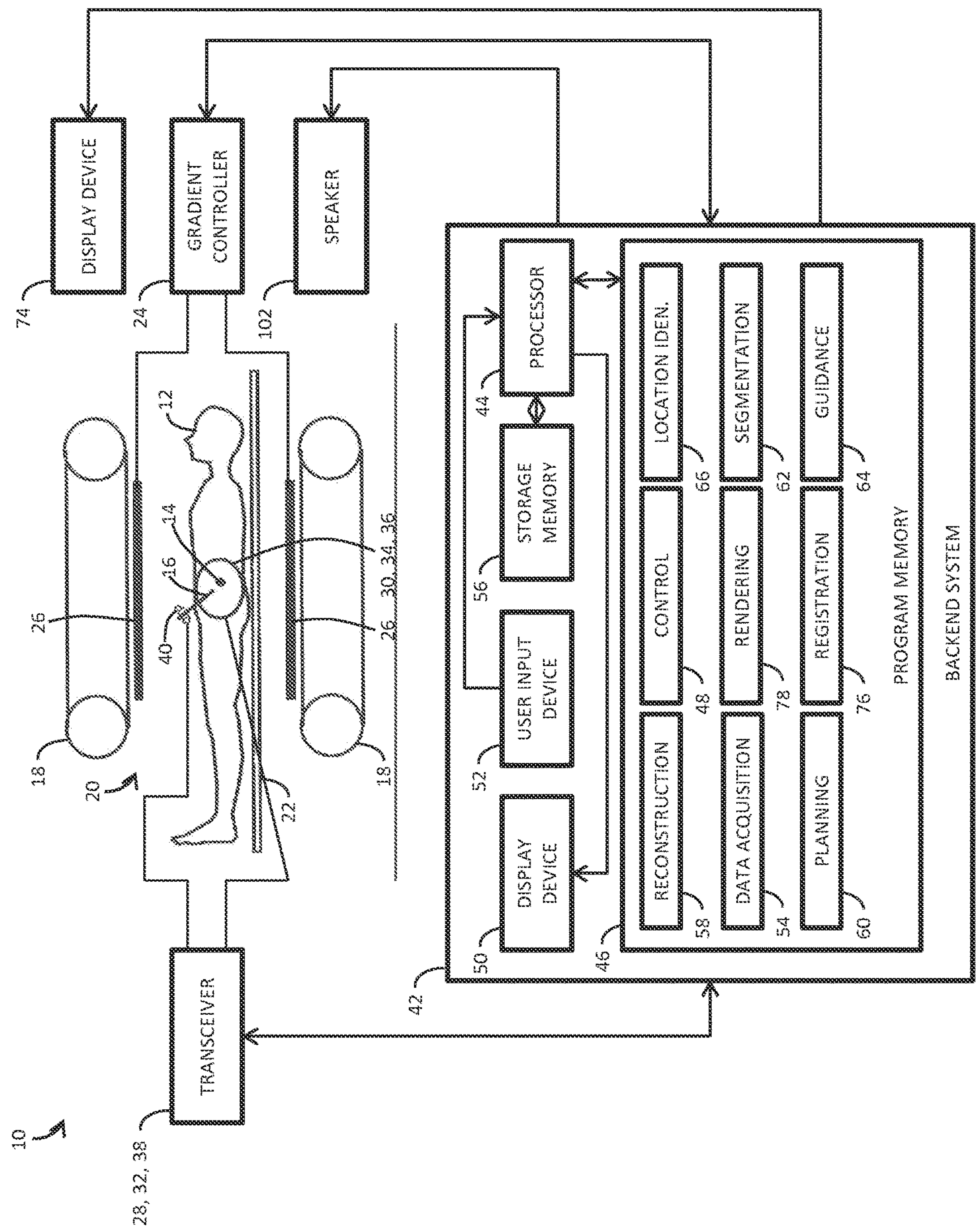
FIG. 1 illustrates a MR system for MR-guidance.

With reference to FIG. 1, a magnetic resonance (MR) system 10 utilizes MR to form two- and/or three-dimensional MR images of a target 14 within a subject 12 and MR for guidance of a shaft or needle 16 to the target 14. The target 14 is, for example, a lesion, such as a tumor. A main magnet 18 creates a strong, static $B_0$ magnetic field extending through an examination volume 20. The examination volume 20 is sized to accommodate the subject 12, which is positioned in the examination volume 20 during imaging and guidance of the shaft or needle 16. An optional support 22 supports the subject 12 and facilitates positioning the subject 12 in the examination volume 20.

The main magnet 18 typically employs superconducting coils to create the the static $B_0$ magnetic field. However, the main magnet 18 can also employ permanent or resistive magnets. Insofar as superconducting coils are employed, the main magnet 18 includes a cooling system, such as a liquid helium cooled cryostat, for the superconducting coils. The strength of the static $B_0$ magnetic field is commonly one of 0.23 Tesla, 0.5 Tesla, 1.5 Tesla, 3 Tesla, 7 Tesla, and so on in the examination volume 20, but other strengths are contemplated.

As illustrated, the main magnet 20 is an open type and includes two superconducting coils spaced apart to define the examination volume 20. The superconducting coils produce the static $B_0$ magnetic field similar to the way in which a Helmholtz coil would. The advantage of an open magnet is that it provides easy access to the subject 12. However, different types of main magnets can also be employed. For example, a split cylindrical main magnet and/or a cylindrical main magnet can be employed. A split cylindrical main magnet is similar to a cylindrical main magnet, which includes a cryostat, except that the cryostat is split into two sections to allow access to the iso-plane of the magnet. Moreover, it is contemplated to employ an interventional instrument other than an MR scanner for generating the real-time images and tracking the shaft or needle 16, such as a computed tomography (CT) scanner.

In the illustrative case of the MR scanner, a gradient controller 24 is controlled to superimpose magnetic field gradients, such as x, y and z gradients, on the static $B_0$ magnetic field in the examination volume 20 using a plurality of magnetic field gradient coils 26. The magnetic field gradients spatially encode magnetic spins within the examination volume 20. Typically, the plurality of magnetic field gradient coils 26 include three separate magnetic field gradient coils spatially encoding in three orthogonal spatial directions.

One or more transmitters 28, such as a transceiver, are controlled to transmit $B_1$ resonance excitation and manipulation radiofrequency (RF) pulses into the examination volume 20 with one or more transmit coils 30, such as one or more of a whole body coil, a surface coil, and a coil of an MR marker. An MR marker is a signal volume wrapped with a coil. The $B_1$ pulses are typically of short duration and, when taken together with the magnetic field gradients, achieve a selected manipulation of magnetic resonance. For example, the $B_1$ pulses excite the hydrogen dipoles to resonance and the magnetic field gradients encode spatial information in the frequency and phase of the resonance signal.

One or more receivers 32, such as a transceiver, are controlled to receive spatially encoded magnetic resonance signals from the examination volume 20 and demodulate the received spatially encoded magnetic resonance signals to MR data. To receive the spatially encoded magnetic resonance signals, the receivers 32 use one or more receive coils 34, such as one or more of a whole body coil, a surface coil and a coil of an MR marker. The receivers 32 typically store the MR data in a buffer memory.

As illustrated, the transmit coils 30 and the receive coils 34 include a surface coil 36 positioned on the surface of the subject 12. The surface coil 36 is employed as both a transmit coil and a receive coil. However, it is to be appreciated that the surface coil 36 can be employed as only one of a transmit coil and a receive coil. Likewise, the receivers 28 and the transmitters 32 include a transceiver 38, which is employed for transmitting and receiving. However, it is to be appreciated that the transceiver 38 can be employed as only one of a transmitter and a receiver.

Further, as illustrated, the transmit coils 30 and/or the receive coils 34 include a coil of an MR marker 40. The shape of the signal volume and the coil of the MR marker 40 are adapted to determine a point on the shaft or needle 16 or a point on the subject 12 where the shaft or needle 16 should be placed without having to remove the marker 40. In the illustrated embodiment, the coil is wrapped around a toroidal signal volume of the MR marker 40, and the MR marker 40 is mounted on the shaft or needle 16 with the shaft or needle 16 extending through the center of the toroidal signal volume. As discussed below, the MR marker 40 can be used determine the location of the shaft or needle 16 or the location of a needle entry point on the subject.

A backend system 42 (e.g., a computer or other electronic data processing device) coordinates the generation of two- or three-dimensional MR images of the target 14 and the guidance of the shaft or needle 16 to the target 14. The backend system 42 includes at least one electronic processor 44 (e.g., a microprocessor, microcontroller, or so forth) and at least one program memory 46. The program memory 46 includes processor executable instructions that, when executed by the processor 44, coordinate the generation and the guidance. The processor 44 executes the processor executable instructions to coordinate the generation and the guidance. In some embodiments, the backend system 42 is implemented as a computer executing a program stored in program memory (i.e., non-transitory storage medium) embodied as a hard disk or other magnetic storage medium, or an optical disk or other optical storage medium, or random access memory (RAM), read-only memory (ROM), or other electronic storage medium, various combinations thereof, or so forth.

A control module 48 of the processor executable instructions controls the overall operation of the backend system 42. The control module 48 suitably displays a graphical user interface (GUI) to a user of the backend system 42 using a display device 50 of the backend system 42. Further, the control module 48 suitably allows the user to interact with the GUI using a user input device 52 of the backend system 42. For example, the user can interact with the GUI to instruct the backend system 42 to coordinate the generation and/or the guidance.

To generate an MR image of the target 14, a data acquisition module 54 of the processor executable instructions acquires MR data of the target 14. The data acquisition module 54 controls the transmitters 28 and/or the gradient controller 24 to implement one or more imaging sequences within the examination volume 20. An imaging sequence defines a sequence of $B_1$ pulses and/or magnetic field gradients that produce spatially encoded MR signals from the examination volume 20. Further, the data acquisition module 54 controls the receivers 32 to acquire the spatially encoded MR signals as MR data. The MR data is typically stored in at least one storage memory 56 of the backend system 42. After acquiring the MR data, a reconstruction module 58 of the processor executable instructions reconstructs the MR data into the MR image of the target 14. The MR image is typically stored in the storage memory 56.

To guide the shaft or needle 16, a planning module 60 of the processor executable instructions generates one or more diagnostic MR images of the target 14, as described above. The trajectory of the shaft or needle 16 is then planned on the diagnostic MR images from an entry point on the surface of the subject 12 to the target 14. The target 14 and the entry point can be identified in the diagnostic MR images using a segmentation module 62 of the processor executable instructions. The segmentation module 62 can perform the identification automatically and/or manually. As to the former, any number of known segmentation algorithms can be employed. As to the latter, the diagnostic MR images are displayed on the GUI and the user identifies the target 14 and/or the entry point in the diagnostic MR images.

After planning, a guidance module 64 of the processor executable instructions determines the current location of the shaft or needle 16 in real-time using a location identification module 66 of the processor executable instructions. The location identification module 66 employs an image based approach or a non-image based approach to determine the location of the shaft or needle 16. As to the former, real-time MR images of the target 14, discussed below, are be analyzed to identify the current location of the shaft or needle 16. For example, the shaft of needle 16 can be formed of a material easily detectable in the real-time MR images and/or the segmentation module 62 can be employed to identify the shaft or needle 16 in the real-time MR images. As to the latter, fiducial markers, such as electromagnetic transponders or MR markers, can be employed. An MR marker is a signal volume wrapped with a coil.

Figure 2:
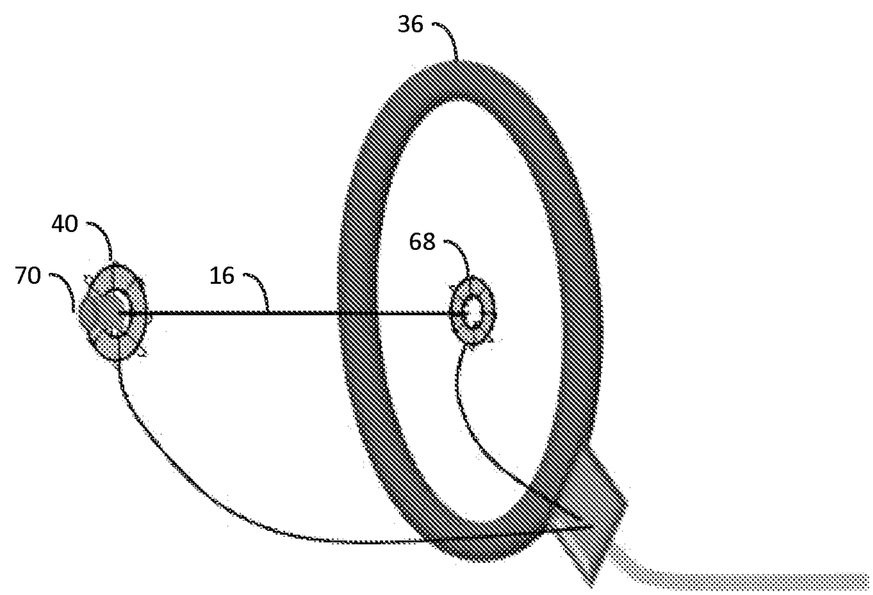
FIG. 2 illustrates an arrangement of MR markers for determining the location of a shaft or needle.

With reference to FIG. 2, and continued reference to FIG. 1, the MR marker 40 is employed as an MR guide marker. Further, an optional MR skin marker 68 is adhered to the surface of the subject 12 with the open center positioned over the planned entry point. The shaft or needle 16 can then be inserted into the subject 12 through the MR skin marker 68. The MR guide marker 40 can optionally be equipped with light sources, such as white light emitting diodes (LEDs), to illuminate along the axis of the shaft or needle 16. If the MR guidance marker 40 has a small diameter, this is only possible if the fingers are proximal to the MR guide marker 40 (e.g., at a needle hub 70 of the shaft or needle 16), since shadowing occurs otherwise.

To determine the location of the shaft or needle 16 using the MR markers 40, 68, the location identification module 66 employs the data acquisition module 54 to acquire MR location data using the MR markers 40, 68 as receive coils. The data acquisition module 54 controls the transmitters 28 and/or the gradient controller 24 to implement one or more tracking sequences using the MR markers 40, 68. A tracking sequence defines a sequence of $B_1$ pulses and/or magnetic field gradients that produce spatially encoded MR signals from the examination volume 20. The tracking sequences can be interleaved with one or more imaging sequences. Further, the data acquisition module 54 controls the receivers 32 to acquire the spatially encoded MR signals as MR location data. The location identification module 66 then processes the MR location data to determine the location of the shaft or needle 16 and of the needle entry point.

Figure 3:
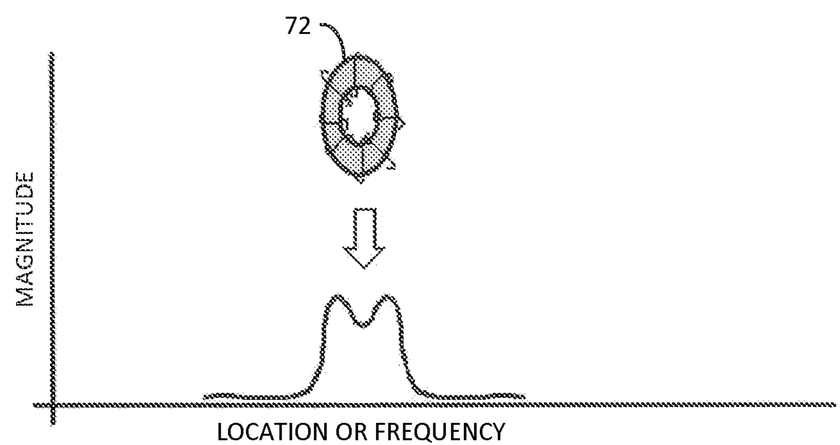
FIG. 3 illustrates an example of how to identify the location of a shaft or needle using an MR marker.

With further reference to FIG. 3, an example of how to identify the location of an MR marker 72, such as the MR guide marker 40 or the MR skin marker 68, using one-dimensional gradient techniques is provided. A gradient is applied in a particular direction, and MR signals are measured using the MR marker 72 in response to $B_1$ pulses. The resulting curve is then plotted, where the y-axis corresponds to signal magnitude and the x-axis corresponds to location or frequency. Since a single gradient field is used, the frequency corresponds to location. The dip in the curve corresponds to the location of the MR marker 72. The use of the MR skin marker 68 advantageously provides some "built-in" spatial registration between the shaft or needle 16 and the patient; however, the MR skin marker 68 is optionally replaced by a marker located at a second location on the shaft or needle 16 (i.e., the second location being different from the location of the MR guide marker 40). If the interventional instrument is other than an MR scanner, then the markers should be chosen to be detectable by that other interventional instrument modality.

Referring to FIG. 1, the guidance module 64 further generates MR images of the target 14, as described above, in real-time. Suitably, the one or more imaging sequences used to generate the real-time MR images are different than the one or more imaging sequences used to generate the diagnostic MR images. The real-time MR images are displayed in real-time to the interventionist on a display device 74 positioned proximate to the subject 12. In displaying the real-time MR images, one or more slices of the real-time MR images, such as two nearly perpendicular slices, which intersect the planned trajectory, are displayed. For example, para-transversal and para-coronal slices are typically displayed for liver procedures. Suitably, the displayed slices are color coded such that each slice is assigned a color.

The real-time MR images are suitably displayed with the location of the planned trajectory overlaid on the real-time MR images. A registration module 76 of the processor executable instructions is suitably employed to transform the location of the planned trajectory to the coordinate frame of the real-time MR images. Further, a rendering module 78 of the processor executable instructions is suitably employed to overlay a representation of the planned trajectory, such as a line, on the real-time MR images.

With reference to FIGS. 4A-D, slices of real-time MR images which can be displayed to an interventionist on the display device 74 are provided. FIGS. 4A and 5B illustrate two nearly perpendicular slices of a real-time MR image acquired during a liver intervention. The planned trajectory of the shaft or needle 16 is illustrated as a line spanning from the skin entry point to the target 14. FIGS. 4C and 4D illustrate two nearly perpendicular slices of another real-time MR image after the shaft or needle 16 has been inserted into the subject 12.

Figure 5:
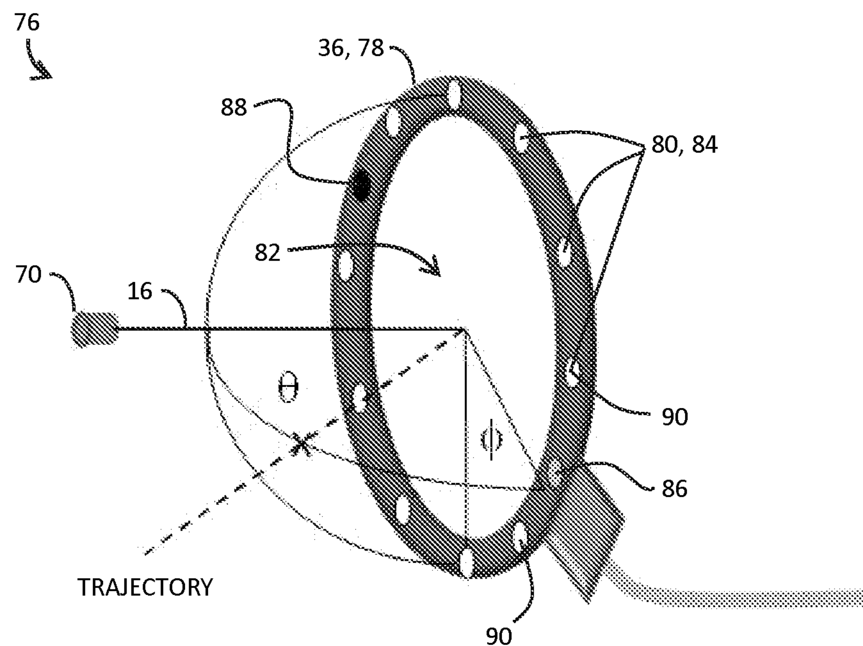
FIG. 5 illustrates positioning a shaft or needle using a user interface for MR-guidance.

Referring back to FIG. 1, and with additional reference to FIGS. 5-9, the guidance module 64 employs a user interface 76 to allow the interventionist to intuitively adjust the slices of the real-time images displayed on the display device 74, as well to intuitively visualize geometries of the shaft or needle 16 in relation to the planned trajectory and the planes of the slices. As illustrated in FIG. 5, the user interface 76 is integrated with and/or secured to the surface coil 36. However, it is to be appreciated that surface coil 36 is not required, whereby the user interface can be employed independent of the surface coil 36.

The user interface 76 includes a frame 78 and a plurality of visual indicators 80, such as LEDs or other light sources, LCD elements or an annular LCD display, or so forth, optionally including touch screen capabilities, mounted to the frame 78. The illustrative visual indicators 80 are light sources 80 (e.g., LEDs). The light sources 80 are arranged around an opening 82 of the frame 78, which can, for example, be annular in shape. For ease of discussion, the light sources 80 are assumed to be arranged in a circle around the opening 82. However, those skilled in the art will appreciate that other shapes are amenable, such as a square, a rectangle, an oval, and so on. Typically, the light sources 80 include 36 light sources and/or illuminate towards the center of the opening 82. Proper blinds to block direct light can avoid blinding the interventionist. The user interface 76 further includes a plurality of user input devices 84, such as buttons or touch screens (e.g., one for each of the light sources 80). The user input devices 84 are integrated with (as illustrated), or positioned proximate to, the corresponding light sources on the frame 78.

In an alternative embodiment, a single touch screen display device, such as a ring-shaped piece of touch screen, replaces the light sources 80 and the user input devices 84. This advantageously moves away from the discreet character of the foregoing embodiments and therefore allows even more accurate or sophisticated means for guidance and manipulation.

During guidance, the interventionist positions the user interface 76 on the surface of the subject 12, where the opening 82 of the frame 78 is positioned over the planned entry point for the shaft or needle 16. The interventionist further positions the tip of the shaft or needle 16 on the entry point. The interventionist can determine the entry point by monitoring the real-time MR images on the display device 74. For example, an appendage, such as a finger, is moved within the field of view of the real-time MR images and to the entry point shown on the real-time MR images, as shown in FIGS. 4A and 4B. Alternatively, two pairs of light sources can be used to provide the location of the planned entry point on the subject 12 to the interventionist. A first pair of light sources lights up in a first color, where the two light sources define a first line on the surface of the subject 12. A second pair of light sources lights up in a second color, where the two light sources define a second line on the surface of the subject 12. The light sources are selected such that the intersection of the first and the second line marks the planned entry point on the subject.

Figure 6:
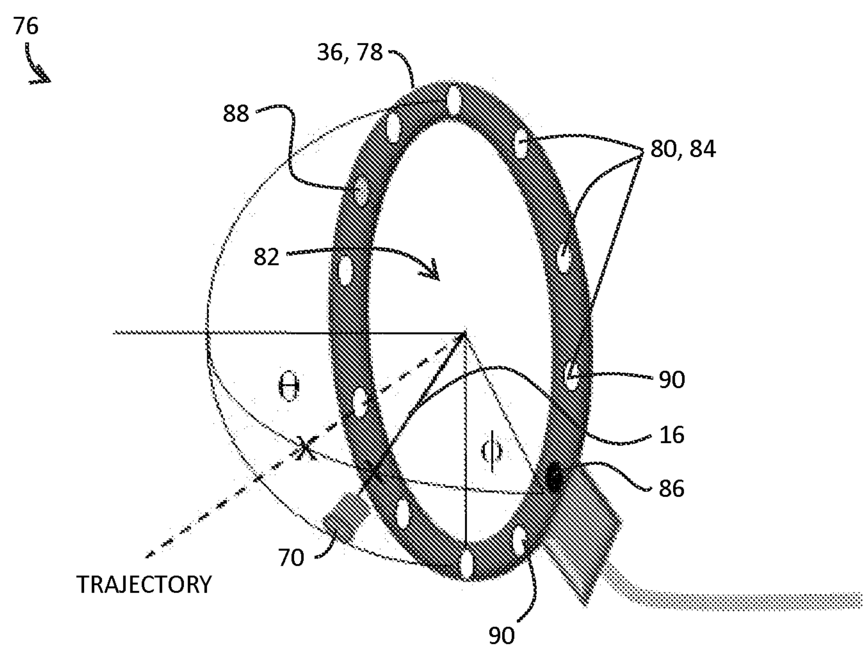
FIG. 6 illustrates positioning a shaft or needle using a user interface for MR-guidance.
Figure 7:
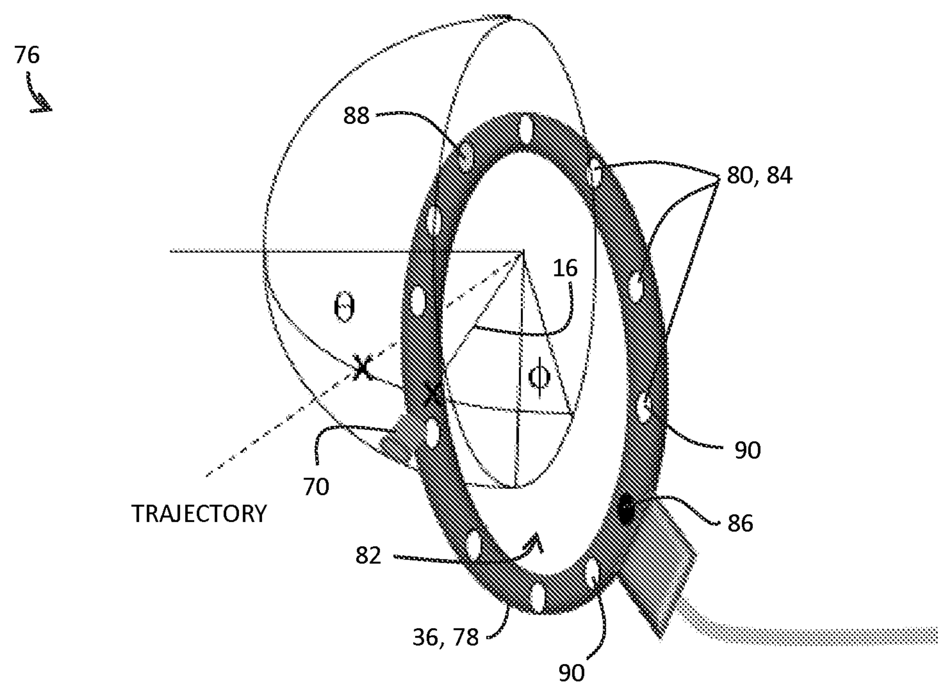
FIG. 7 illustrates positioning a shaft or needle using a user interface for MR-guidance where the entry point is not arranged in the center of the circular arrangement.

Using the planned trajectory, the guidance module 64 calculates target angles $\varphi_t$ and $\theta_t$ for the planned trajectory in a polar coordinate system. The coordinate system is centered at the entry point, which may not necessarily coincide with the center of the circular arrangement of light sources 80. The plane $\theta=\pi$ of the coordinate system is defined by the plane of the circular arrangement of light sources 80. Further, using the current location of the shaft or needle 16, the guidance module 64 calculates angles $\varphi$ and $\theta$ for the shaft or needle 16 in polar coordinates. The angles $\varphi$ and $\theta$ of the shaft or needle 16 are illustrated in FIGS. 5-7.

To calculate the angles, the location of the user interface 76 on the subject 12 is determined. Where the user interface 76 is integrated with and/or secured to the surface coil 36, the position of the user interface 76 can be determined using a reference scan, such as a SENSE reference scan. A reference scan is a lowly resolved three-dimensional scan with wide field of view (FOV). The data acquisition module 54 is suitably employed to carry out the reference scan. It controls the transmitters 28 and/or the gradient controller 24 according to the one or more imaging sequences of the reference scan. Further, the data acquisition module 54 controls the receivers 32 to acquire spatially encoded MR signals from both a whole body receive coil and the surface coil 36. The reconstruction module 58 is then employed to generate a magnitude MR image from the ratio of both signals, which corresponds to the sensitivity profile of the surface coil 36.

The guidance module 64 can then use the magnitude image to determine the location of the surface coil 36 since magnitude is largest in the vicinity of the coil leads. This determination can be done by fitting a model of the surface coil 36 to the maximum of the magnitude image with an appropriate cost function. Where the surface coil 36 is circular, three translational and three rotational fit parameters are required. The model can be extended by a curvature radius if the coil bends to, for example, small subjects. If the arrangement of the light sources 80 has some mirror- or rotation-symmetry, it is additionally required to define a reference point on the user interface 76 to uniquely identify the position of the light sources 80.

Where the MR guide marker 40 and/or the MR surface marker 68 are employed to determine the location of the shaft or needle 16, the reference point can be identified by fixing the MR guide marker 40 or, where applicable, the MR skin marker 68 on one of the light sources 80 during the reference scan and triggering the respective user input device. The guidance module 54 can then evaluate the position of the MR marker from the reference scan to identify the position of the triggered user input device. Alternatively, the reference point can be identified by fixing the MR guide marker 40 or, where applicable, the MR skin marker 68 on one of the light sources 80 during a tracking sequence and triggering the respective user input device. The guidance module 54 can then evaluate the position of the MR marker from the MR data to identify the position of the triggered user input device. In both instances, the need to trigger the respective user input device can be removed by visually marking the reference light source and always putting the MR marker on this light source while determining the reference point.

Based on the angles, the guidance module 64 adjusts the light sources 80 to provide a visual indication as to where the interventionist needs to move the shaft or needle 16 to align the shaft or needle 16 to the planned trajectory. Additionally or alternatively, the light sources 80 provide a visual indication of the deviation of the current position of the shaft or needle 16 (as determined from the real-time localization of the markers 40, 68) from the planned trajectory. Visual cues to the interventionist can be made by varying the color, brightness, or other like properties of the light sources 80. Visual cues to the interventionist can also be made by flashing the light sources 80 and varying the frequency with which the light sources 80 flash. One approach for indicating alignment of the shaft or needle 16 is as described below.

If only a small number of light sources is provided on the circular arrangement, in general, none of them will be positioned precisely at the target angle $\varphi_t$. In this case of a small number of light sources, the following approach is used to still enable the interventionist to accurately guide the shaft of needle 16 to the desired target angle $\varphi_t$. The approach employs the two light sources 90 which are left and right adjacent to the light source 86 at $\varphi_t$. They remain dark as long as $\varphi=\varphi_t$. If $\varphi>\varphi_t$, the color of that light source 90 which is located at a smaller angle $\varphi$ is set to yellow. The other light source 90 at a larger angle $\varphi$ is turned off. If $\varphi<\varphi_t$, the color of that light source 90 which is located at a larger angle $\varphi$ is set to yellow, and the other light source 90 at a smaller angle is turned off. As similarly described above for the angle $\theta$, the yellow light source 90 indicates that the interventionist must move the shaft or needle in the direction of this light source to approach $\varphi_t$. As the interventionist moves $\varphi$ towards $\varphi_t$, the intensity of the yellow light source 90 gradually decreases towards zero. Effectively, the interventionist nulls the brightness of the two adjacent light sources 90 when the shaft or needle 16 arrives at the target angle $\varphi_t$. Since the human eye can precisely determine a brightness null, the target angle can be precisely approached.

As illustrated in FIGS. 5-7, the angle $\theta$ of the shaft of needle 16 is out of alignment with the angle $\theta_t$ of the planned trajectory. In FIG. 5, $\theta<\theta_t$. Hence, the color of the light source 86 located at $\varphi_t$, is set to green and the color of the opposite light source 88 is turned off. In FIGS. 6 and 7, $\theta>\theta_t$. Hence, the color of the light source 86 located at $\varphi_t$ is turned off and the color of the opposite light source 88 is set to green. All other light sources may be set to white to illuminate the scene.

Where $\varphi\neq\varphi_t$, the color of the light source which is farthest from the light source located at $\varphi$ and which is adjacent the light source 86 located at $\varphi_t$ is set to white. The other light source which is adjacent to the light source 86 located at $\varphi_t$ is set off. Where $\varphi=\varphi_t$, the color of the light sources 90 adjacent the light source 86 located at $\varphi_t$ are set to off. The white light source indicates that the interventionist must move the shaft or needle in the direction of the white light source. As the interventionist moves $\varphi$ towards $\varphi_t$, the intensity of the white light source increases towards maximum intensity. As the interventionist moves $\varphi$ away from $\varphi_t$, the intensity of the white light source increases towards maximum intensity. Effectively, the interventionist nulls the brightness of the two adjacent light sources 90 when the shaft or needle 16 arrives at the target angle $\varphi_t$. Since the human eye can precisely determine a brightness null, the target angle can be precisely approached.

The above described approach for indicating alignment has the advantage that it works if the planned trajectory is close to the north pole (i.e., $e\theta_t\approx 0$). However, if $\theta_t$ is below a certain threshold, the adjacent light sources 90 can be switched off to avoid confusing the interventionist by erratically flashing the light adjacent sources 90. Even more, the above described approach advantageously works if the entry point is not arranged in the center of the circular arrangement, as illustrated in FIG. 7. Further, the light sources 80 advantageously illuminate the entry point and provide intuitive guidance to align the shaft or needle 16. Sterile drapes with transparent foil sections at the user interface 76 can be used to cover the user interface 16 and the subject 12.

Based on the angles, the guidance module 64 further adjusts the light sources 80 to provide a visual indication as to position of the one or more slices of the real-time MR images displayed on the display device 74 positioned proximate to the subject 12. MR operators are used to identifying different slices by different color codes. Hence, it is advantageous to reuse this color coding to visualize the cross section of the slices. For each slice displayed, the corresponding light sources are set to the color coding the slice.

Further, based on the angles, the guidance module 64 further allows the interventionist to manipulate the position of slices displayed on the display device 74. As noted above, each of the light sources 80 is associated with a user input device, such as a button. One approach for manipulating the slice positions is as described below. However, it is to be appreciated that numerous variants are possible.

Triggering the user input device (e.g., single clicking a button) associated with one of the light sources indicating the position of a slice selects the slice for manipulation. Selection can be indicated by, for example, higher brightness or flashing of the two light sources. Triggering the user input device (e.g., single clicking a button) associated with one of the light sources indicating the position of the selected slice deselects the slice.

Once a slice is selected, the slice can be rotated by triggering a user input device on one side of a line spanning between light sources indicating the slice. Selecting a user input device in the clockwise direction rotates the slice by a predefined angle step in the clockwise direction, and triggering a user input device in the counter clockwise direction rotates the slice by a predefined angle step in the counter clockwise direction. If the number of user input devices on the user interface 76 is high enough, this may be perceived as if dragging the slice. Further, once the slice is selected, the slice can be shifted and tilted by triggering a user input device on the other side of the line spanning between the light sources indicating the slice. A single trigger (e.g., a single click of a button) of one of these user input devices shifts the slice in the direction of the user input device, and a double trigger (e.g., a double click of a button) tilts the slice in a predetermined direction about the line.

Figure 8:
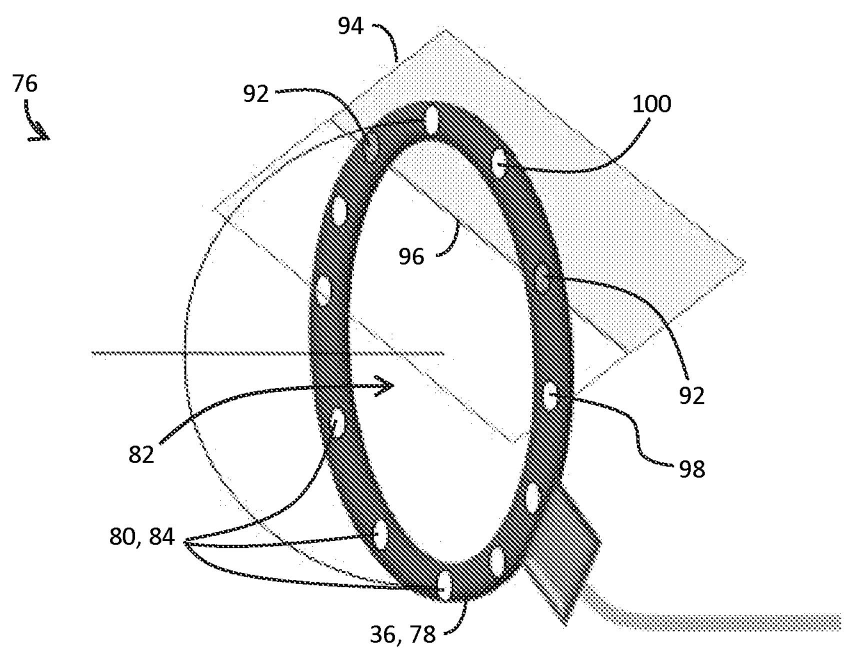
FIG. 8 illustrates displaying the position of a slice using a user interface for MR-guidance.
Figure 9:
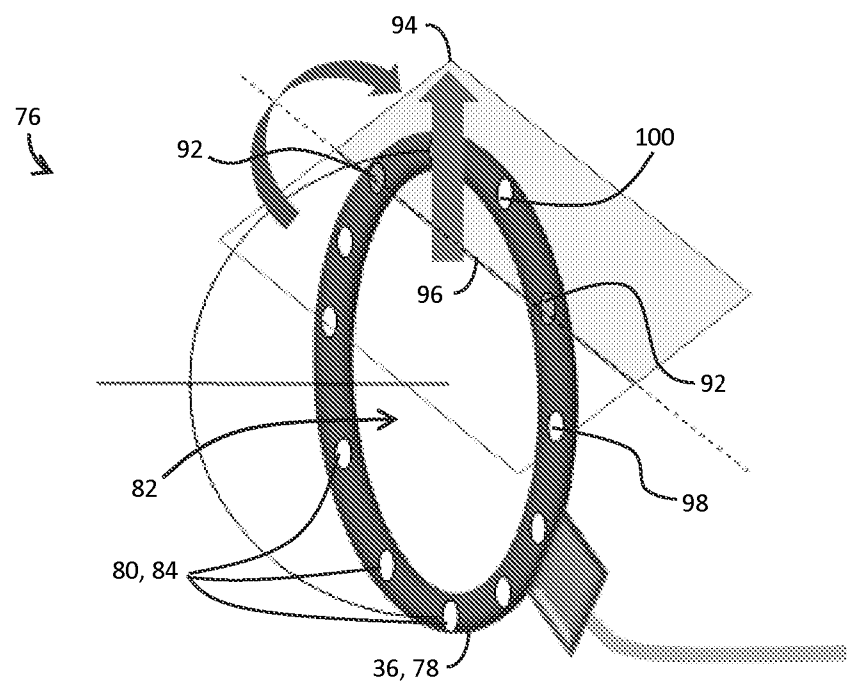
FIG. 9 illustrates rotating and shifting a slice using a user interface for MR-guidance.

As illustrated in FIGS. 8 and 9, two light sources 92 indicate the cross section of a slice 94 coded blue and displayed on the display device 74. Triggering a user input device 98 on one side of a line 96 spanning between the two light sources rotates the slice 94. Single triggering a user input device 100 on the other side of the line 96 shifts the slice 94, and double triggering the user input device 100 on the other side of the lien 96 tilts the slice 94.

In addition to, or as an alternative, to the user interface 76, the guidance module 64 can employ audio signals to guide the interventionist in adjustment of the trajectory of the shaft or needle 16. Parameters like the pitch of the tone, the duration of the tone or a suitably generated beat signal with a reference tone can be used to indicate the distance of the shaft or needle 16 from the planned trajectory. The audio signals can be presented to the interventionist using, for example, an electroacoustic transducer 102, such as a speaker. In addition to, or as an alternative, to the user interface 76, the guidance module 64 can employ a display device positioned on, for example, the surface coil 36 which numerically presents the deviation of the current trajectory of the shaft or needle 16 from the planned trajectory.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes at least one memory and at least one processor, the processor executing processor executable instructions on the memory; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A user interface system for guidance of a shaft or needle to a target of a subject, said user interface system comprising:

a user interface including:

a frame configured to be positioned on a surface of a subject disposed in an examination volume of an associated magnetic resonance (MR) system, the frame including an opening over an entry point of a planned trajectory for the shaft or needle, the planned trajectory extending from the entry point to the target; and, visual indicators arranged on the frame around the opening, the visual indicators including a plurality of light sources spaced around the opening; and at least one processor programmed to:

determine a position of the user interface using a reference scan performed by the MR system;

determine a current trajectory of the shaft or needle using MR images of the subject acquired by the associated MR system;

compare the planned trajectory with the current trajectory to determine the deviation of the shaft or needle from the planned trajectory; and, generate a visual indication of the deviation of the shaft or needle from the planned trajectory using the one or more visual indicators of the user interface.

2. The system according to claim 1, wherein the one or more visual indicators include a display device surrounding the opening, and wherein the visual indication is generated by selectively displaying visual cues on the display device around the opening to indicate a direction of proper alignment of the shaft or needle relative to the planned trajectory.

3. The system according to claim 1, wherein the at least one processor is programmed to generate the visual indication by at least one of:

selectively turning the one or more visual indicators on and/or off to indicate a direction of proper alignment of the shaft or needle to the planned trajectory; and, selectively adjusting one or more of color, brightness, and flashing frequency of the one or more visual indicators to indicate the direction of proper alignment.

4. A user interface system for guidance of a shaft or needle to a target of a subject, said user interface system comprising:

at least one processor programmed to display a real-time slice on a display device of real-time MR images of a subject disposed in an examination volume of an associated magnetic resonance (MR) system, the real-time MR images being acquired by the associated MR system; and, a user interface including:

a frame configured to be positioned on a surface of the subject disposed in the examination volume of the associated MR system, the frame including an opening over an entry point of a planned trajectory for the shaft or needle, the planned trajectory extending from the entry point to the target; and, one or more visual indicators arranged on the frame around the opening;

wherein the at least one processor is further programmed to determine a position of the user interface using a reference scan performed by the MR system and to generate a visual indication of the current position of the displayed real-time slice using the one or more visual indicators of the user interface to indicate where the plane of the displayed real-time slice intersects the frame.

5. The system according to claim 4, wherein the processor is further programmed to:

monitor the user input devices to detect triggering of a user input device; and, in response to detecting triggering of the user input device, adjust the current position of the displayed real-time slice based on position of the triggered user input device.

6. The system according to claim 4, wherein the one or more visual indicators include a plurality of light sources spaced around the opening, and wherein each of the one or more visual indicators corresponds to a different one of the user input devices.

7. The system according to claim 4, wherein the displayed real-time slice is one of a plurality of color coded slices displayed on the display device, and wherein the one or more visual indicators indicate where the plane of the displayed real-time slice intersects the frame using the color coding of the displayed real-time slice.

8. The system according to claim 4, wherein the user interface is integrated with a surface transmit and/or receive coil.

9. The system according to claim 1, further including an electroacoustic device outputting an audio signal indicating the deviation of the shaft or needle from the planned trajectory.

10. The system according to claim 1, wherein the at least one processor is programmed to: using the one or more visual indicators, visually indicate deviation of the shaft or needle from the planned trajectory and visually indicate the current position of the real-time slice.

11. An apparatus operating in conjunction with an associated magnetic resonance (MR) system or computed tomography (CT) scanner providing real time imaging for guiding a shaft or needle to a target of a subject, the apparatus comprising:

a frame configured to be positioned on a surface of the subject, the frame including an opening over an entry point of a planned trajectory for the shaft or needle extending from the entry point to the target, the frame comprising a ring that encircles the opening and including one or more visual indicators arranged on the frame and encircling the opening; and at least one processor programmed to operate the one or more visual indicators on the frame to visually indicate at least one of: (i) a current position of the shaft or needle determined based on the real time imaging performed by the associated MR system or CT scanner; and (ii) deviation of the current position of the shaft or needle determined based on the real time imaging performed by the associated MR system or CT scanner from the planned trajectory.

12. The apparatus according to claim 11, wherein the one or more visual indicators are one of (1) a set of LEDs encircling the opening and (2) an annular display encircling the opening.

13. The system according to claim 1, wherein the at least one processor is programmed to generate the visual indication by selectively adjusting all of color, brightness, and flashing frequency of the one or more visual indicators to indicate the direction of proper alignment of the shaft or needle to the planned trajectory.

14. The system according to claim 1, further comprising:

an MR skin marker configured to be adhered to the surface of the subject, and configured to allow the shaft or needle to be inserted through the MR skin marker to the subject, wherein the MR skin marker comprises a receive coil.

15. The system according to claim 14, further comprising an MR guide marker comprising:

a receive coil; and light emitting diodes configured to illuminate along an axis of the shaft or needle.

* * * * *